United States Patent
Robitaille et al.

(10) Patent No.: US 7,128,872 B2
(45) Date of Patent: Oct. 31, 2006

(54) METHOD AND APPARATUS FOR OZONE STERILIZATION

(75) Inventors: Simon Robitaille, Charny (CA); Mario Simard, St. Jean (CA); Stephane Fournier, Levis (CA); Sylvie Dufresue, Cap Rouge (CA); Richard Turcot, Cap Rouge (CA)

(73) Assignee: TSO3 Inc., Quebec (CA)

( * ) Notice: Subject to any disclaimer, the term of this patent is extended or adjusted under 35 U.S.C. 154(b) by 704 days.

(21) Appl. No.: 10/005,786

(22) Filed: Nov. 8, 2001

(65) Prior Publication Data

US 2002/0085950 A1    Jul. 4, 2002

Related U.S. Application Data

(63) Continuation-in-part of application No. 09/310,695, filed on May 12, 1999, now abandoned.

(30) Foreign Application Priority Data

Apr. 30, 1999 (CA) ................................. 2270512

(51) Int. Cl.
- A61L 9/00 (2006.01)
- A61L 2/00 (2006.01)
- A62B 7/08 (2006.01)
- C01B 13/10 (2006.01)
- C25C 1/00 (2006.01)

(52) U.S. Cl. ................... 422/28; 422/1; 422/4; 422/22; 422/24; 422/105; 422/121; 422/186.7; 204/176; 204/194; 205/626; 205/334; 205/752; 205/756; 205/615

(58) Field of Classification Search ................... 422/1, 422/4, 22, 24, 28, 105, 121–123, 186, 186.08, 422/186.07, 292, 295, 296, 305, 906–907, 422/33, 116; 204/176, 194; 205/626, 334, 205/752, 756, 615

See application file for complete search history.

(56) References Cited

U.S. PATENT DOCUMENTS

| | | | | |
|---|---|---|---|---|
| 3,719,017 A | * | 3/1973 | Shapiro | 53/431 |
| 4,687,635 A | | 8/1987 | Kaehler et al. | |
| 4,770,851 A | * | 9/1988 | Joslyn | 422/26 |
| 5,069,880 A | * | 12/1991 | Karlson | 422/186.19 |
| 5,344,622 A | * | 9/1994 | Faddis et al. | 422/306 |
| 5,656,246 A | * | 8/1997 | Patapoff et al. | 422/187 |
| 5,702,669 A | * | 12/1997 | Green | 422/30 |
| 5,868,999 A | | 2/1999 | Karlson | |
| 6,284,193 B1 | * | 9/2001 | Carman et al. | 422/33 |
| 6,325,972 B1 | * | 12/2001 | Jacobs et al. | 422/33 |

FOREIGN PATENT DOCUMENTS

| | | |
|---|---|---|
| WO | WO 99/32162 | 7/1999 |
| WO | WO 00/66186 | 11/2000 |
| WO | WO 01/58499 | 8/2001 |

OTHER PUBLICATIONS

Patent Abstracts of Japan; vol. 1995, No. 08, Sep. 29, 1995 and JP 07 136236 A (Iwatate Iryo Kikai Seisakusho:KK), May 30, 1995, Abstract.

* cited by examiner

*Primary Examiner*—Gladys JP Corcoran
*Assistant Examiner*—Monzer R. Chorbaji
(74) *Attorney, Agent, or Firm*—Akerman Senterfitt; Stephan A. Pendorf (57) ABSTRACT

The sterilization method disclosed includes the steps of
providing a sterilization chamber;
placing the article into the sterilization chamber;
equalizing the temperature of the article and the sterilization atmosphere;

sealing the sterilization chamber;
applying a vacuum of a preselected vacuum pressure to the sterilization chamber;
supplying water vapour to the sterilization chamber under vacuum;
supplying ozone-containing gas to the sterilization chamber;
maintaining the sterilization chamber sealed for a preselected treatment period; and
releasing the vacuum in the sterilization chamber;
whereby a vacuum pressure is used which lowers the boiling temperature of water in the sterilization chamber below the temperature in the sterilization chamber. One or more ventilating cycles can be added to the preferred method for removing the remaining ozone and humidity from the sterilization chamber. Single cycle sterilization with ozone is more efficient and provides for a shorter sterilization cycle than with ETO and requires few changes in user habits. Moreover, the ozone-based process in accordance with the invention is compatible for use with current packaging, such as sterile pouches and rigid containers. The sterilization process is simple and substantially avoids human errors caused by false interpretation and handling. The ozone sterilization method of the invention requires substantially no aeration or cooling down of sterilized instruments so that they can be used immediately following the sterilization cycle. This allows hospitals to reduce the cost of maintaining expensive medical device inventories.

12 Claims, 5 Drawing Sheets

METHOD AND APPARATUS FOR OZONE STERILIZATION

RELATED U.S. APPLICATION

This application is a continuation-in-part of Ser. No. 09/310,695, filed May 12, 1999 now abandoned, entitled "METHOD AND APPARATUS FOR OZONE STERILIZATION," pending, the disclosure of which is incorporated herein by reference.

FIELD OF THE INVENTION

The invention relates to sterilization equipment and, particularly, to a method and apparatus for ozone sterilization.

BACKGROUND OF THE INVENTION

Sterilization is the absolute destruction of any virus, bacteria, fungus or other microorganism, whether in a vegetative or in a dormant spore state. Conventional sterile processing procedures for medical instruments involve high temperature (such as steam and dry heat units) or toxic chemicals (such as ethylene oxide gas, EtO). Steam pressure sterilization has been the time-honoured method of sterilization. It is fast and cost effective. However, the autoclave destroys heat-sensitive instruments. Thus, since more and more heat-sensitive instruments such as arthroscopes and endoscopes are used in medical treatment, other types of sterilization need to be used.

Ethylene oxide sterilization is used to cold sterilize heat-sensitive instruments. Until recently, ethylene oxide sterilization was the state of the art method for cold sterilization. Ethylene oxide sterilizes heat and moisture-sensitive objects and penetrates very well. However, it has been deemed by national health and safety organizations to be carcinogenic and neurotoxic. Additionally, since it is a highly flammable gas, it is normally combined with CFCs (chlorofluorocarbons) for safety reasons. However, due to the deleterious effects of CFCs on the ozone layer, their use has been banned by the Montreal protocol in 1996. Moreover, ethylene oxide requires long sterilization and aeration periods, since the molecule clings to the surface of instruments. The total sterilization time is 14 to 36 hours depending upon the materials to be sterilized. This type of sterilization necessitates the use of containment rooms, monitoring systems, and room ventilators.

A more efficient, safer, and less expensive sterilization agent was needed and has been found in the form of ozone $O_3$ which is the fourth most powerful, but overall most desirable oxidizing agent (the three more powerful agents being fluorine derivatives which are too unstable and toxic for safe use in sterilization). Ozone can easily be generated from oxygen, especially hospital grade oxygen. Oxygen is readily available in the hospital environment, usually from a wall or ceiling oxygen source, or, if mobility is required, from a portable "J" cylinder of oxygen.

Ozone is widely used in industry as oxidizing agent to bleach paper pulp, treat drinking water, and sterilize sewage water and food products. Ozone generally acts on chemical compounds in two ways. Either by direct reaction or through hydroxyl radical species formed during the decomposition of ozone (Encyclopaedia Of Chemical Technology, Vol. 17, Ozone page 953 to 964). The amounts (concentrations) of ozone required in the sterilization gas for water purification are low, generally less than 36 mg/l (milligram per liter). However, significantly higher concentrations are required to make ozone gas an effective sterilant of micro-organisms, those high concentrations of ozone gas have to be combined with critical levels of humidity during the entire sterilization cycle. The activity of ozone increases rapidly with increased relative humidity. The resistance of spores to ozone varies from strain to strain, but the differences become comparatively small at high relative humidity (Ishizaki et al., 1986. Inactivation of the Silas spores by gaseous ozone, J. Appl. Bacterial, 60:67–72). A high relative humidity is required for the ozone to penetrate the protective shells of microorganisms. The presence of water often accelerates ozone reactions with organic substances (Langlais et al., (EDS), 1991, Ozone in Water Treatment, Application and Engineering. Louis Publishers: Chelsea, Mich., 569 pages). Sufficient relative humidity is also required in order to enable ozone to penetrate the normally used sterilization packaging. Thus, it is desirable to humidify this ozone gas used for sterilization applications.

Various ways of humidifying ozone-containing gas used for sterilization treatments are known in the field of ozone sterilizers.

The use of a mixture of ozone gas with a very fine water mist in a sealed plastic bag container, which contains an article to be sterilized, is described in U.S. Pat. No. 3,719,017. The method disclosed involves repeated evacuation and refilling of the plastic bag with a mixture of ozone gas and a very fine water mist. The air in the bag is exhausted and replaced with a pressurized mixture of ozone and water mist. Upon encountering the much lower pressure within the bag, the water particles from the pressurized mixture explode, forming a water mist. However, this system cannot generate a sufficiently high water vapour concentration to provide and maintain the required high relative humidity.

A review of more recent patents shows that the relative humidity required for successful sterilization is at least 85% throughout the process. U.S. Pat. No. 5,069,880 describes a device capable of generating such a high relative humidity. In the apparatus described, the ozone gas is bubbled through a water bath in an effort to increase the water content of the gas. Although ozone at 85% humidity can kill most micro-organisms, it does not meet the "worst case scenario" stipulated in North American standards. Moreover, the device described is unable to generate humidity levels higher than 85%.

North American standards set by agencies such as the Food and Drug Administration and Heath Canada require sterilizer manufacturers to meet worst-case scenario requirements. A sterilization gas including 85% humidity is insufficient for achieving the targeted results. A minimum relative humidity level of 95% is required to meet the standards imposed.

Water evaporates at 100° C. at atmospheric pressure (1013 mbar). Thus, various prior patents (see Faddis et al., U.S. Pat. Nos. 5,266,275; 5,334,355; and 5,334,622) teach sterilization systems wherein water is heated to above the boiling point to produce steam for injection into the ozone-containing gas produced by an ozone generator. The steam is heated to 120° C. Thus, the vapour/ozone mixture used for sterilization presumably has a temperature close to 100° C. However, since the decomposition of ozone increases exponentially with temperature in the range of 20 to 300° C., injecting the water vapour at a temperature of about 120° C. leads to premature ozone decomposition. As a result, the effective ozone concentration in the gas produced by the ozone generator is reduced, thereby requiring significantly increased treatment times and the generation of much larger amounts of ozone gas for each sterilization cycle. On the other hand, if the temperature in the sterilization chamber is not maintained at above the boiling temperature of water, condensation will occur. However, a layer of condensation on any article to be sterilized will significantly reduce the effectiveness of the ozone sterilization process, if not completely block sterilization of the covered area. This problem should be avoided, but is not recognized in the art.

Moreover, carrying out the sterilization at an elevated temperature and close to 100° C. will require a substantial cooling down period for the sterilized materials, thereby making the sterilization a lengthy and inefficient process. Thus, a more efficient and effective sterilization method and apparatus is desired for the sterilization with ozone at a relative humidity above at least 95%.

SUMMARY OF THE INVENTION

It is an object of the invention to provide a method and apparatus for the sterilization of an article with ozone-containing gas, wherein the ozone-containing gas is humidified with water vapour at a relative humidity above 85%, preferably at the saturation point and a temperature at or close to room temperature.

It is another object of the invention to provide a sterilization method and apparatus for ozone sterilization wherein the sterilization is carried out with humidified ozone-containing gas having a temperature of 25 to 40° C.

It is still another object of the invention to provide an ozone sterilization method and apparatus wherein the sterilization is carried out at a temperature substantially equal to room temperature for allowing removal of the sterilized articles immediately after completion of the sterilization cycle, thereby avoiding extended cool-down periods.

It is yet a further object of the invention to provide an ozone sterilization method and apparatus wherein the sterilization period is significantly reduced by using an ozone-containing sterilization gas having a relative humidity above 85%, preferably about 100%.

It is still a further object of the invention to provide an ozone sterilization method and apparatus wherein condensation of water from the sterilization atmosphere during the sterilization process is substantially prevented.

These objects are achieved with a method and apparatus in accordance with the invention wherein sterilization is carried out under vacuum, whereby the vacuum pressure is selected such that the boiling temperature of water in the sterilization chamber is below the temperature inside the sterilization chamber and at about room temperature so that substantially all water in the sterilization chamber is maintained in the vapour phase at all times.

In a preferred embodiment of the method and apparatus in accordance with the invention, a vacuum pressure is applied to lower the boiling point of water below the temperature inside the chamber. This vacuum pressure is preferably between 0.1 and 10 mbar, most preferably between 0.5 and 2.0 mbar.

The preferred sterilization method in accordance with the invention for the sterilization of an article includes the following steps:

providing a sterilization chamber;
placing the article into the sterilization chamber;
sealing the sterilization chamber;
equalizing the temperature of the article and the atmosphere in the sterilization chamber,
applying a vacuum of a preselected vacuum pressure to the sterilization chamber;
supplying water vapour to the sterilization chamber under vacuum;
supplying ozone-containing gas to the sterilization chamber;
maintaining the sterilization chamber sealed for a preselected treatment period; and
releasing the vacuum in the sterilization chamber, whereby a vacuum pressure is used which lowers the boiling point of water in the sterilization chamber below the temperature in the sterilization chamber.

Although equalization of the temperature of the article and the sterilization chamber can be achieved by simply waiting sufficiently long, this may results in undesired delay of the sterilization procedure and is also hard to detect. Thus, temperature equalization is preferably achieved by applying a series of equalization pulses wherein vacuum is applied to the chamber, followed by the injection of ambient air or oxygen. This will result in the chamber, the articles and the atmosphere in the chamber all being at the same temperature prior to commencement of the actual sterilization with ozone, in particular about the same temperature as the ambient air.

Preferably, heat is applied during the sterilization cycle to the chamber, the door, the humidifier and the water vapour piping to maintain them at a preselected temperature, most preferably the temperature of ambient air.

One or more ventilating cycles can be added to the preferred method for removing the remaining ozone and humidity from the sterilization chamber.

Accordingly, a sterilization apparatus in accordance with the invention includes a sterilization chamber;
means for equalizing the temperature of the sterilization chamber, any materials placed therein, and an atmosphere in the sterilization chamber;
means for supplying ozone-containing gas to the sterilization chamber;
means for supplying water vapour to the sterilization chamber; and
means for applying a sufficient vacuum to the sterilization chamber to lower the boiling temperature of water below the temperature inside the sterilization chamber.

Application of a sufficient vacuum to lower the boiling point of water to below the temperature in the sterilization chamber results in evaporation of water into the humidifier. The water vapour is then admitted into the chamber until saturation is reached. The energy required for this evaporation is taken from the water itself and any components of the apparatus in contact with that water in the liquid phase. The result is a temperature drop in the humidifier, which may lead to a decrease in the evaporation rate and possibly even some ice formation. In the chamber the high relative humidity level combined with temperature differentials between walls and/or the load may lead to water condensation. Thus, the apparatus in accordance with the invention preferably further includes means for heating at least one of the chamber, an access door of the chamber, the humidifier and the water vapour piping.

BRIEF DESCRIPTION OF THE DRAWINGS

The invention will be described in more detail in the following by way of example only and with reference to the attached drawings wherein.

DETAILED DESCRIPTION OF THE PREFERRED EMBODIMENT

Figure 1:
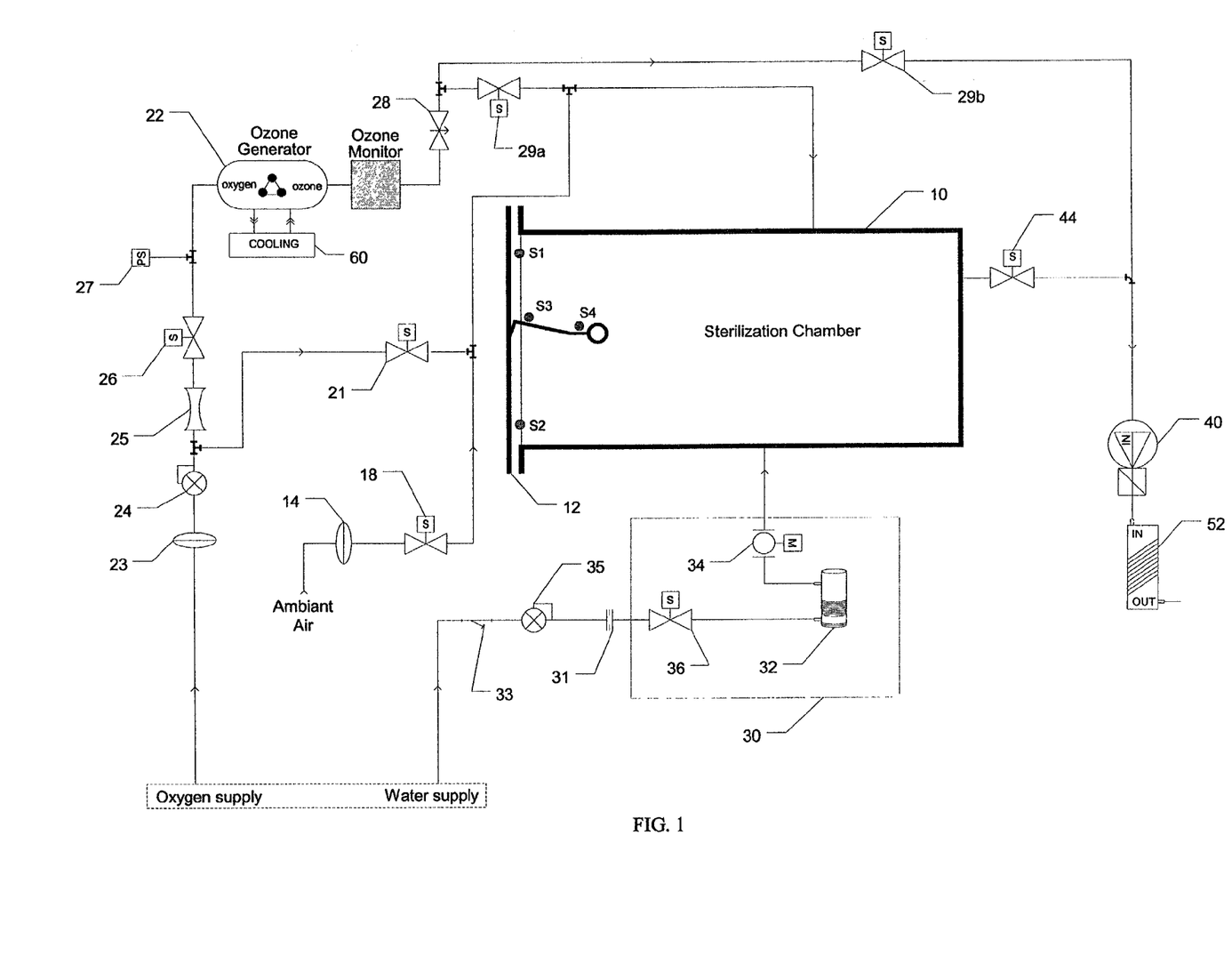
FIG. 1 shows a schematic illustration of an apparatus in accordance with the invention.

An ozone sterilizer in accordance with the invention as illustrated schematically in FIG. 1 operates in a relatively simple manner. Medical quality oxygen is subjected in an ozone generator 22 to an electrical field, which converts the oxygen into ozone containing gas. The ozone containing gas is then fed into a humidified sterilization chamber 10 where it sterilises medical devices. The ozone is subsequently reconverted into oxygen using an ozone catalyst 52. The only residues left at the end of the sterilization cycle are oxygen and clean water.

Single cycle sterilization with ozone is more efficient and provides for a shorter sterilization cycle than sterilization with ETO and requires few changes in user habits. Moreover, the ozone-based process in accordance with the invention is compatible for use with current packaging, such as sterile pouches and rigid containers.

The sterilization process of the invention is simple and substantially avoids human errors caused by false interpretation and handling.

The ozone sterilization method of the invention requires substantially no aeration or cooling down of sterilized instruments so that they can be used immediately following the sterilization cycle. This allows hospitals to reduce the cost of maintaining expensive medical device inventories. The ozone sterilization method of the invention offers several further advantages. It produces no toxic waste, does not require the handling of dangerous gas cylinders, and poses no threat to the environment or the user's health. Stainless-steel instruments and heat-sensitive instruments can be treated simultaneously, which for some users will obviate the need for two separate sterilizers.

Prior art ozone sterilization apparatus and methods exist in which the sterilization atmosphere is humidified to increase the efficiency of the ozone sterilization process. However, the relative humidity respectively achieved is insufficient (at most 85%) to maximize the effect of the ozone containing sterilization gas. Furthermore, it has now been surprisingly discovered by the inventors of the present process and apparatus that sterilization at a relative humidity above 80% and especially close to 100% creates additional challenges associated with unwanted condensation on articles to be sterilized and/or components of the sterilization apparatus which are exposed to the sterilization atmosphere. In particular, it has been found that even slight differences in temperature between the atmosphere in the sterilization chamber and the articles to be sterilized or the atmosphere and components of the apparatus will trigger significant condensation when the relative humidity in the chamber is close to saturation. However, since it is desired for maximum efficiency of the ozone sterilization to operate as closely as possible to saturation and to avoid condensation on the articles to be sterilized, at least prior to ozone injection, such temperature differences should be avoided as much as possible. The process and apparatus in accordance with the invention provides a simple and effective solution to this problem by equalizing, prior to the actual sterilization process, the temperature of all materials exposed to the atmosphere in the sterilization chamber. This is preferably achieved through repeated evacuation of the chamber and intermediate flushing with ambient air or oxygen at ambient temperature. Of course, temperature equalization can be achieved in many other ways, including simply waiting sufficiently long for equalization to occur automatically through radiation or convection.

The preferred sterilization apparatus in accordance with the invention as illustrated schematically in FIG. 1 includes a sterilization chamber 10 which can be sealed to contain a vacuum. This is achieved with an access door 12, which can be selectively opened for access into the chamber and which seals the chamber in the closed condition. The apparatus further includes an ozone generator 22 for supplying ozone-containing gas to the sterilization chamber, a humidifier arrangement 30 for supplying water vapour to the sterilization chamber, and a vacuum pump 40 (SP500-B, manufacturer Anest Iwata). The vacuum pump 40 is used for the application of a sufficient vacuum to the sterilization chamber 10 to increase the penetration of the sterilizing gas and to be able to generate water vapour at a temperature below the temperature inside the sterilization chamber. The vacuum pump 40 in the preferred embodiment is capable of producing a sufficient vacuum in the sterilization chamber to lower the boiling point of water in the chamber below the actual temperature of the atmosphere in the chamber. In the preferred apparatus, the vacuum pump is capable of producing a vacuum of 0.1 mbar. Ozone produced in the ozone generator 22 is destroyed in an ozone catalyst 52 to which ozone-containing gas is fed either after passage through the sterilization chamber 10 or directly from the ozone generator 22 through valve 29*b* (optional). The ozone catalyst 52 (DEST 25, manufacturer TSO3) is connected in series after the vacuum pump 40 to prevent ozone gas escaping to ambient. The ozone decomposing material in the preferred catalyst 52 is carulite. For economic and practical reasons, it is preferred to use a catalyst for decomposition of the ozone in the sterilization gas exhausted from the sterilization chamber 10. The catalyst destroys ozone on contact and retransforms it into oxygen with a certain amount of heat being produced. Catalysts of this type and their manufacture are well known to the person skilled in the art of ozone generators and need not be described in detail herein. Furthermore, other means for destroying the ozone contained in the sterilization gas will be readily apparent to a person skilled in the art. For example, the gas can be heated for a preselected time to a temperature at which the ozone decomposition is accelerated, for example, to 300° C.

The humidifier arrangement 30 includes a humidifier chamber 32 (HUM 0.5, manufacturer TSO3) sealed to ambient and connected to the sterilization chamber 10 through a conduit and a vapour intake valve 34. The humidifier chamber 32 is equipped with a level control to always ensure a sufficiently high water level (not shown). Water is directly supplied to the humidifier chamber 32 from a drinking or purified water supply connection. Water is supplied to the humidifier chamber 32 by way of a filter 33, a pressure regulator 35, an orifice 31 and input valve 36. The water vapour produced in the humidifier chamber 32 enters the sterilization chamber 10 by way of a vapour intake valve 34. The humidifier chamber is also preferably equipped with a heating device (not shown) that maintains the temperature of the water sufficiently high to achieve a higher water vapour evaporation rate.

Figure 5:
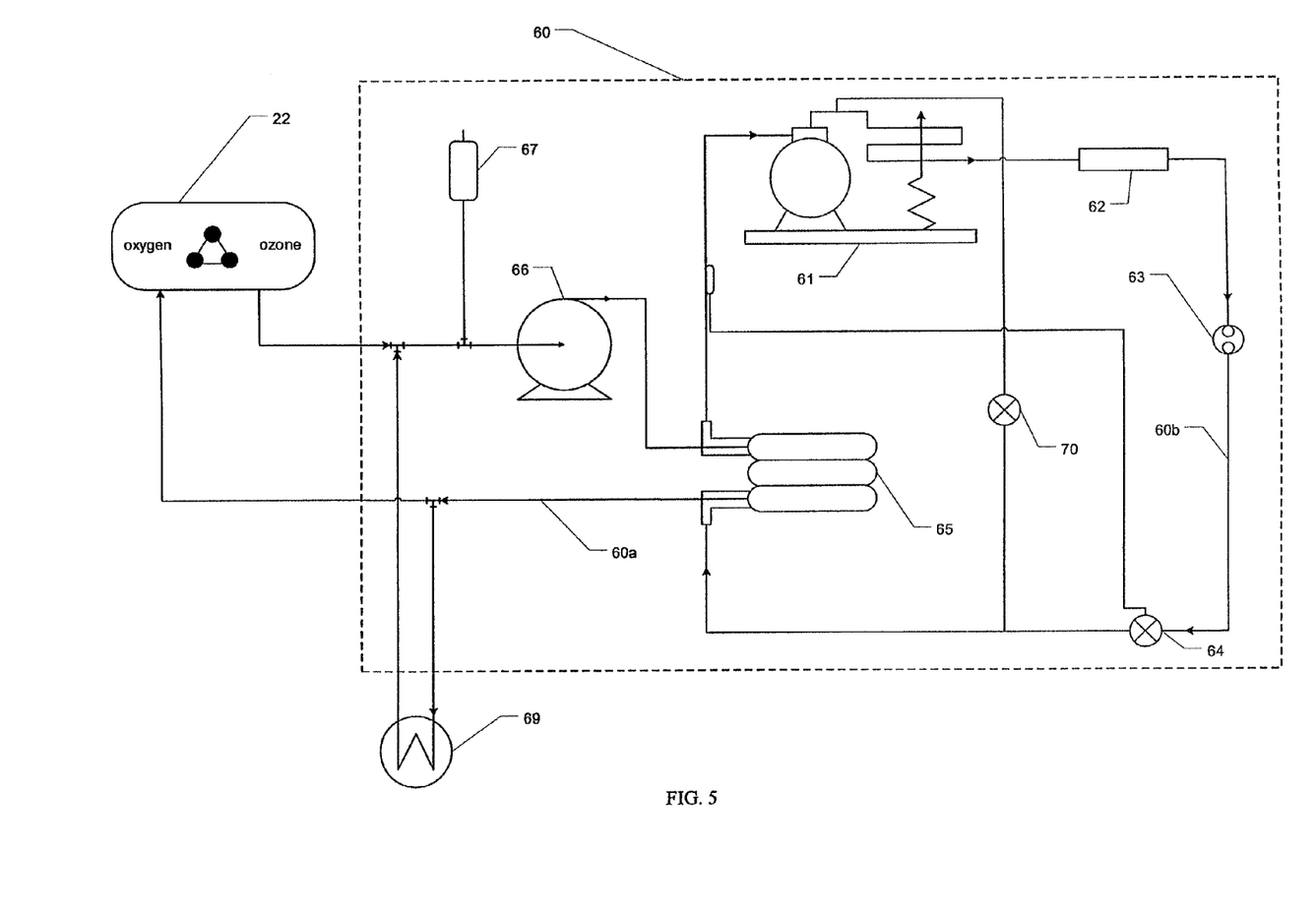
FIG. 5 is a schematic illustration of the cooling unit of the apparatus in accordance with the invention.

The ozone generator 22 (OZ, model 14a, manufacturer TSO3) is of the corona discharge type and is cooled to decrease the ozone decomposition rate, all of which is well known in the art. To achieve a good lethality rate in an ozone sterilization process, the ozone supplied in the sterilization chamber should be sufficient to obtain a concentration of 48 to 96 milligram per liter preferably 60 to 85 milligram per liter. At these concentrations, the ozone generation is associated with a relatively high-energy loss in the form of heat. Generally, about 95% of the supplied electrical energy is converted into heat and only 5% is used to produce ozone. Since heat accelerates the inverse transformation of ozone into oxygen, it should be removed as quickly as possible by cooling of the ozone generator 22. The ozone generator in the apparatus is kept at the relatively low temperature of 3 to 6° C. by either an indirect cooling system 60 as illustrated in FIG. 5 with cooling water recirculation, or a direct cooling system with a refrigeration unit for cooling (not illustrated). The cooling system is preferably kept at the temperature of 3 to 6° C. In the preferred embodiment, the cooling system is kept at 4° C. so that the ozone-containing gas generated by generator 22 is at the ambient temperature of around 20 to 35°C. Thus, the ozone-containing gas entering into the sterilization chamber for humidification and sterilization is kept at ambient temperatures of 20 to 35° C. This means that ozone decomposition is minimized and that the sterilization process is more efficient. This provides a significant advantage over the apparatus in the prior art, since the temperature and pressure are maintained low throughout the sterilization cycle.

The ozone-generating unit 50 is preferably supplied with medical grade oxygen. The apparatus can be connected to a wall oxygen outlet common in hospitals or to an oxygen cylinder or to any other source capable of supplying the required quality and flow. The supply of oxygen to the generator 22 takes place across a filter 23, a pressure regulator 24, a flow meter 25 and an oxygen shut off valve 26. The generator is protected against oxygen over pressure by a safety pressure switch 27. The ozone-oxygen mixture generated by the generator 22 is directed to the sterilization chamber 10 by a regulator valve 28 and a mixture supply solenoid valve 29a. The mixture can also be directly supplied to the ozone catalyst 52 by way of a bypass solenoid valve 29b (optional). In the preferred embodiment which includes a sterilization chamber of 125 liters volume, the pressure regulator 24 and the regulator valve 28 preferably controls the oxygen input at a pressure of about 116.5 kPa (2.2 psig) and a flow rate of about 1.5 liters per minute. However, it will be readily apparent to the skilled person that other flow rates may be used depending on the make and model of the ozone generator 22 and the size of the sterilization chamber.

The apparatus in accordance with the invention preferably includes a closed circuit cooling system using absolutely no fresh water (see FIG. 5). The cooling liquid flowing inside the generator 22 is a glycol-water mixture, which is cooled using R134a, an ozone layer friendly refrigerant. The cooling system is capable of maintaining a temperature of 3 to 6° C. and preferably 4° C. The cooling system 60 of the generator 22 as shown in the schematic diagram of FIG. 5 includes a condensing unit 61 (Copelaweld FTAH-B074, manufacturer: Copeland), a drier 62 (UK-O53S, manufacturer: Alco), a sight glass 63 (optional) (ALM-1TT3, manufacturer: Alco), an expansion device 64 (Danfoss TUAE, orifice #4, manufacturer: Danfoss), an evaporator 65 (Packless COAX-2151-H, manufacturer: Packless), a hot gas bypass 70 (ADRI 1-1/4, manufacturer: Sporlan) a circulation pump 66 well known to the person skilled in the art, and an expansion reservoir 67 (Amtrol ST-5, manufacturer: Amtrol). The cooling unit 60 is divided into a heat transfer circuit 60a and a refrigerating circuit 60b. The heat transfer circuit 60a includes the ozone generator 22, the high voltage circuit cooler 69, the coolant side of the evaporator 65, the circulation pump 66 and the expansion reservoir 67 (optional). The refrigeration circuit 60b includes the condensing unit 61, the drier 62, the sight glass 63, the expansion device 64, hot gas bypass 70 and the refrigerant side of the evaporator 65. The refrigerant circulating in the refrigeration circuit is R134a and the coolant flowing in the heat transfer circuit 60a is a glycol/water mixture.

The heat transfer circuit 60a can be omitted and the generator 22 included directly in the refrigeration circuit 60b. However, the use of an intermediate glycol/water filled heat transfer circuit is preferred, since the additional coolant acts as a larger heat sink so that energy peak loads generated upon activation of the generator 22 can be more reliably handled without significant swings in the temperature of the oxygen/ozone gas mixture produced.

The vacuum in the sterilization chamber 10 is produced by the vacuum pump 40 and the sterilization chamber drainage valve 44.

Valves 18, 21, 26, and 36 are all the same (model: 0211-A-06,0-FF-VA-NM82-120/60-08, manufacturer: Burkert). Valves 29a and 29b are Teflon solenoid valves (model: SV-2-1447-C, manufacturer: Parker). Valve 34 is preferably a solenoid valve which is the same model as the vacuum valve 44 (model: L9942302, manufacturer: Varian).

Figure 2:
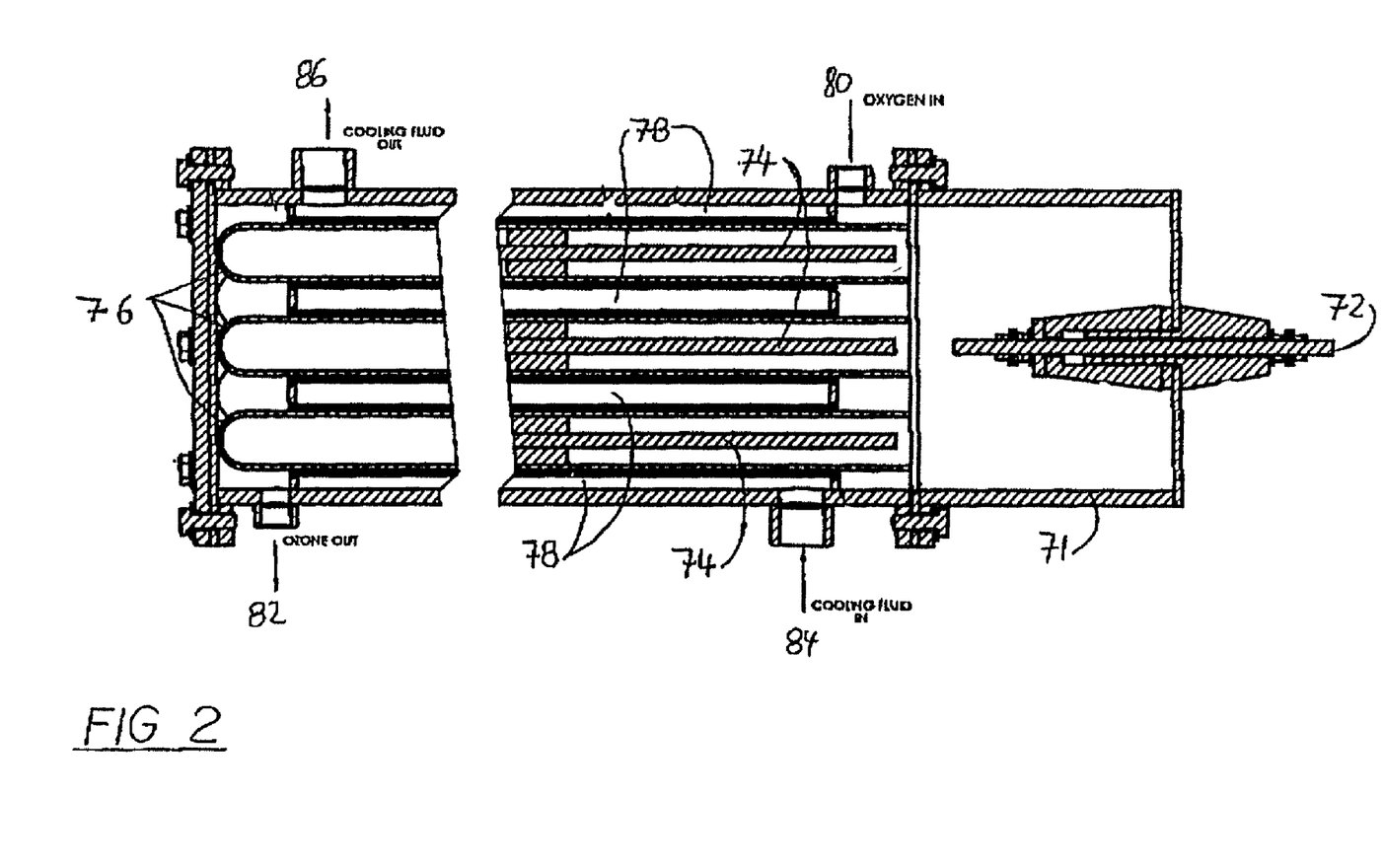
FIG. 2 is a cross-section through a preferred ozone generator used in an apparatus in accordance with the invention.

The preferred ozone generator used in the process and apparatus of the invention is schematically illustrated in FIG. 2 and is a generator of the corona discharge type well known to the person skilled in the art. The generator includes a first electrode 72 and a number of second electrodes 74 respectively centrally positioned in one of a corresponding number of reaction tubes 76. An ozone generating zone is defined between each second electrode 74 and the associated reaction tube 76. The electrodes are high voltage electrodes. Either electrode may be the ground electrode. The reaction tubes 76 are respectively surrounded by a cooling liquid channel 78 for cooling of the tubes. Oxygen enters the generator at an oxygen inlet 80 and ozone exits the generator at an ozone outlet 82. The reaction tubes are preferably made of a dielectric material, for example glass. The generator further includes an outer pressure vessel or housing 71 in which the oxygen inlet 80, ozone outlet 82 are provided as well as a cooling liquid inlet 84 and a cooling liquid outlet 86.

Operation

Figure 3:
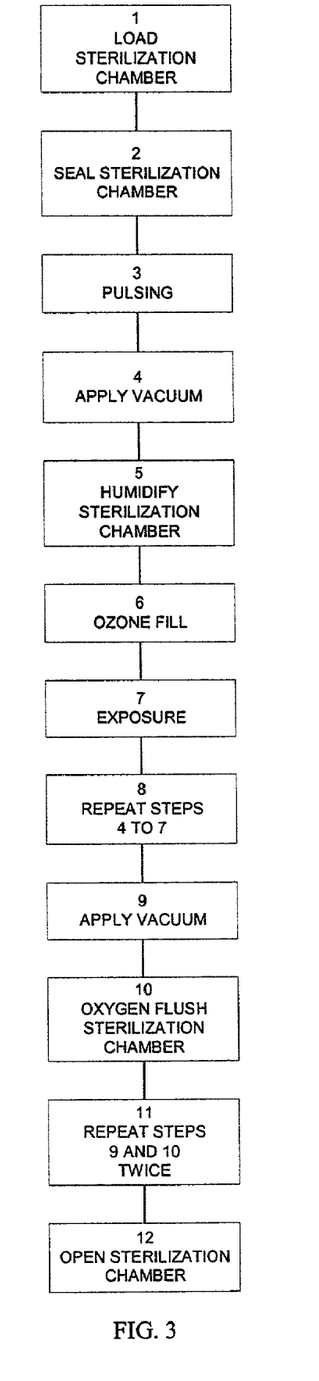
FIG. 3 is a flow diagram of a preferred method in accordance with the invention.

The preferred sterilization method according to the invention includes the following general steps as illustrated by the flow chart of FIG. 3. The medical instruments to be sterilized are sealed in sterile packaging containers or pouches such as generally used in the hospital environment and then placed into the sterilization chamber. The door of the sterilization chamber is closed and locked and the temperature equalization phase is started. This phase includes repeated pulsing of ambient air or oxygen at ambient temperature through the sterilization chamber. Then, vacuum is applied to the sterilization chamber. Water vapour is admitted into the sterilization chamber to humidify the chamber contents. A mixture of ozone and oxygen is supplied to the chamber and the chamber maintained sealed for a preselected treatment period. The vacuum application and ozone supply steps are preferably repeated at least once. To remove all remaining ozone in the sterilization chamber 10 after the sterilization cycle is completed a ventilation phase is commenced. After the ventilation phase the door is unlocked and the sterilized articles can be removed from the chamber. The temperature of the bottom and door of the chamber, of the water vapour piping and of the humidifier is preferably controlled throughout the sterilization process.

Before the sterilization cycle begins, the humidifier chamber 32 is filled with water to an adequate level. This is done by temporarily opening the water-input valve 36. Valve 36 also preferably opens automatically during the sterilization cycle if the water level is dropping below a preselected limit.

During the first phase of the sterilization cycle, the temperature equalization step, air intake valve 18, oxygen supply valves 21 and 26, mixture supply valve 29a, and mixture bypass valve 29b are closed and vapour intake valve 34 and chamber drainage valve 44 are opened. The sterilization chamber 10 is evacuated to a vacuum pressure of about 330 mbar. Then the chamber drainage valve 44 is closed, intake valve 18 is opened and air is admitted into the chamber until ambient atmospheric pressure is reached. This sequence is repeated 10 times to ensure full temperature equalization.

Thereafter, intake valve 18 is closed, chamber drainage valve 44 is opened and the sterilization chamber 10 is evacuated to a vacuum pressure of about 1.0 mbar. Water vapour inlet valve 34 is closed when the absolute pressure in the sterilization chamber falls below 60 mbar. Once a pressure of about 1.0 mbar is achieved, the chamber drainage valve 44 is closed and the vapour intake valve 34 opened to lower the pressure in the humidifier chamber 32 to the vacuum pressure in the sterilization chamber. That forces the water in the humidifier chamber to evaporate with the resulting water vapour automatically entering the sterilization chamber 10 due to the associated increase in volume. Preferably, during the humidification period, valve 34 opens and closes several times for a pre-set period of time to control the increasing rate of the relative humidity inside the chamber. Instead of using a humidifier chamber, humidity into the chamber could also be achieved with one or many spray nozzles connected to the water supply line. When valve 34 opens the pressure of the water flowing through the nozzle produces a water fog that evaporates into the volume under vacuum. Shortly before the end of the humidification period (usually about 2 to 6 min.), the ozone generator is activated. The flow of the oxygen/ozone mixture exiting the ozone generator is controlled at all times by regulator valve 28 capable of resisting the vacuum and of adjusting the flow to between 1 and 3 liters per minute. As an optional feature, the generator can be started at the same time as the humidification period begins. This is then achieved with supply valve 26 and mixture bypass valve 29b. Supply valve 26 opens to let oxygen enter the generator. The ozone-oxygen mixture produced by the generator is then guided directly into the ozone catalyst 52 through mixture bypass valve 29b. After a humidification period of 30 to 90 minutes, the oxygen-ozone mixture is guided into the sterilization chamber by opening the mixture supply valve 29a and closing the mixture bypass valve 29b. The oxygen-ozone mixture enters the chamber 10 until an ozone concentration of 85 milligram per liter in the chamber is achieved. The time required for this step is dependent on the flow rate and concentration of the ozone gas in the mixture (preferably 150 to 190 mg/l NTP) and the ozone concentration can be monitored with equipment known in the art. Once the desired concentration is reached, the mixture supply valve 29a is closed to seal off the sterilization chamber and to maintain the humidified ozone/oxygen gas mixture in the chamber under vacuum.

Once the sterilization chamber is filled with the sterilization gas (mixture of oxygen and ozone gas), the generator 22 is stopped, the oxygen supply valve 26 is closed, and the ozone is maintained in contact with the articles to be sterilized for about 20 minutes, for a sterilization chamber of a volume of 125 liters (4 cubic feet). The length of the sterilization period varies with the volume of the sterilization chamber. At this stage, the sterilization chamber is still under the effect of a partial vacuum of about 610 mbar. In an optional second step, the pressure level is raised to about 900 mbar using oxygen as a filling gas. This pressure level is maintained for about 20 min. After the sterilization period, the vacuum is reapplied, preferably at a pressure of about 1.0 mbar again. Once the vacuum reaches 1.0 mbar, the humidification phase is recommenced, followed by the renewed injection of an oxygen/ozone sterilization gas mixture, followed by the sterilization period. The cycle of applying a vacuum of about 1.0 mbar, injecting sterilization gas, humidifying and sterilization period, can be repeated, and the number of repeat cycles (mini cycles) selected to achieve complete sterilization of the instruments. The number of repeat cycles needed in an experimental set-up of a method and apparatus in accordance with the invention including a 125 liters (4 cubic foot) chamber was 2. This set-up conformed to the Security Assurance Level standards of the FDA (SAL 10-6).

To remove all remaining ozone and humidity in the sterilization chamber 10 after complete sterilization a ventilation phase is engaged. The ventilation phase begins after the last sterilization period. The chamber drainage valve 44 is opened and a vacuum is applied down to approximately 6.5 mbar. Vapour intake valve 34 closes when the pressure reaches 60 mbar to evacuate the remaining ozone in the humidifier. Once the vacuum pressure of 6.5 mbar is obtained, drainage valve 44 closes and the oxygen supply valve 21 opens, admitting oxygen into the sterilization chamber 10. Once atmospheric pressure is reached, the oxygen supply valve 21 is closed, the sterilization chamber drainage valve 44 is opened, and vacuum reapplied until a pressure of 1.3 mbar is reached. This last ventilation cycle, down to 1.3 mbar, is repeated once for a total of three ventilation cycles. Once atmospheric pressure is reached after the last cycle, the door mechanism of the sterilization chamber is activated to permit access to the contents of the sterilization chamber. The ventilation phase has two functions. First, to remove all ozone residues in the sterilization chamber before opening the access door and, second, to dry the sterilized material by evaporation when the vacuum pressure is applied. Of course, different vacuum pressures, cycle times and number of repetitions can be used, as long as the desired ozone removal and drying are achieved.

The ozone-containing gas evacuated from the sterilization chamber 10 is passed over the ozone catalyst 52 prior to exhausting the gas to the atmosphere to ensure a complete decomposition of the ozone in the sterilization gas. The ozone catalyst 52 is used during only two portions of the sterilization cycle, the activation of the generator 22 (with optional valves 26 and 29b) and the evacuation of the sterilization chamber 10. During the start up phase of the generator 22, the mixture bypass valve 29b is opened and the ozone is guided across the catalyst 52. Once the start-up phase of the generator 22 is complete, the bypass valve 29b closes. During evacuation of the sterilization chamber 10, the sterilization chamber drainage valve 44 is opened and the ozone containing sterilization waste gas is guided to the catalyst 52. Once the evacuation of the sterilization chamber 10 is completed, the drainage valve 44 is closed. The circulation of ozone is ensured by the vacuum pump 40. The ozone catalyst 52 can be located upstream or downstream of the vacuum pump 40.

Control System

Figure 4:
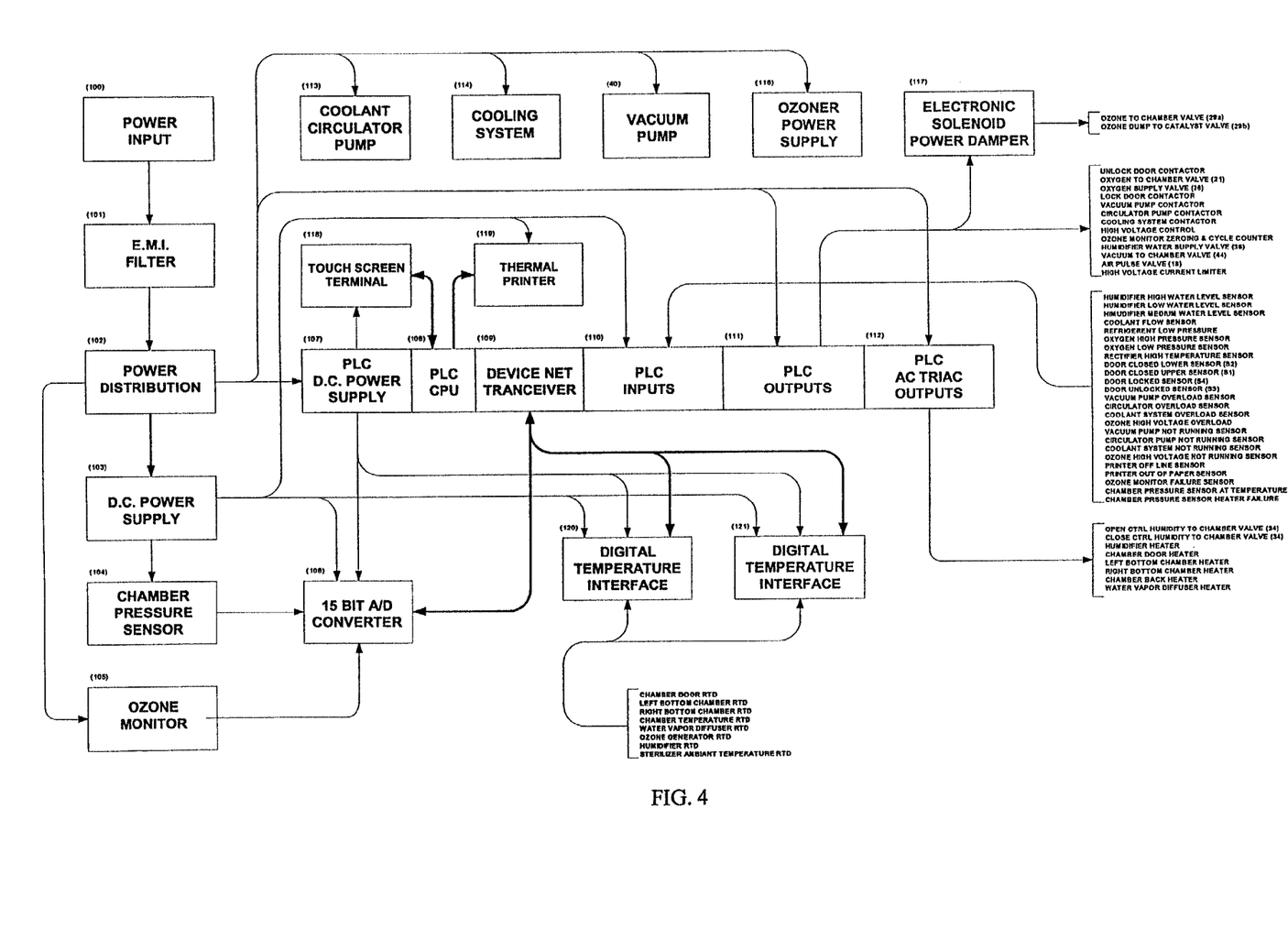
FIG. 4 is a flow diagram of the electrical and control system preferably used in the apparatus of FIG. 1.

The sterilization apparatus is preferably controlled by the scheme presented in the electrical block diagram (FIG. 4 and Process Flow Diagram (FIG. 1). The control system is build around a PLC shelf (Programmable Logic Controller). This shelf contains a power supply (107) a CPU unit (108), a Device Net Transceiver (109), a 32×24 volts DC discrete input module (110), a 16×120VAC discrete output module (111) and finally an 8×120VAC TRIAC controlled output module (112). All those modules are disposed on a physical shelf that contains a data and address bus.

Device Net is an industrial serial communication protocol largely used in the industry for instrumentation and control. In this sterilization apparatus the Device Net transceiver (109) is used to communicate in full duplex, the data between the CPU (109) and the 15 bit A/D converter (106) and both Digital Temperature Interfaces (120), (121).

The PLC CPU posses three RS232 ports. One is used to receive and send data to the Touch Screen Terminal (118), another one is used to send data to a thermal printer (119) and the last port is used as a service port where a PC (Personal Computer) can be hooked up to communicate with the PLC CPU (108) to load up the control protocol program. (Control Protocol Program is not in the scope of this document).

The Touch Screen terminal (118) is located at the front of the sterilizer beside the thermal printer (119). Touch Screen Terminal and thermal printer constitute a User Interface terminal.

Power needed for: "thermal printer (119), Device Net Link, (109), (106), (120), (121), Chamber Pressure Sensor (104) and PLC discrete inputs (111)" come from the DC Power Supply (103).

Chamber Pressure Sensor (104) and Ozone Monitor (105) have standard 0 to 10VDC output signal. Both signals are sent to a 15 bits A/D converter. Then, both converted signals are sent to CPU by the Device net digital link for processing.

Power input (100) of the sterilizer is a four wire 208 VAC 3 phases in star configuration with neutral. The 3-phase power input is filtered to prevent conducted RFI (101). Then, power is distributed by power distribution buss (102) to the various electrical systems of the sterilizer apparatus.

A cooling system (60) is used to cool down the ozone generator. This system includes the cooling unit (114) and the coolant circulator pump (113). The temperature of the coolant in the generator is sense by an RTD located at the generator. The temperature is sent to the CPU (108) by the Device Net system (109) (120) (121). Coolant circulator (113) and cooling unit (114) are controlled by contactors driven by PLC outputs (111), which in turn are controlled of the software protocol. All input and output required to achieve cooling system control are listed on the electrical block diagram as: Circulator Pump Contactor, Cooling System Contactor, Circulator Overload Sensor, Cooling System Overload system, Coolant System Not Running Sensor, Circulator pump Not Running Sensor. Refrigerant Low Pressure and Coolant Flow Switch.

The vacuum control system includes the vacuum pump 40 and a pressure sensor 104. The start and stop operations of the vacuum pump are controlled according to the control protocol. All input and output required for the vacuum system is listed on the diagram: Vacuum Pump Contactor, Vacuum Pump not running sensor, Vacuum pump Overload sensor, Vacuum to Chamber Valve (44), Air Pulse Valve (18) and Oxygen to Chamber Valve (21) The pressure sensor output is converted by the 15 bit A/D converter (106) and sent to the CPU by the Device Net digital Link (109). The pressure sensor also posses two discrete outputs indicating to the CPU (108) the following conditions: Chamber Pressure Sensor at Temperature and Chamber Pressure Sensor Heater failure. Those two signals are listed on the electrical block diagram as PLC inputs.

The sterilization chamber door actuator system includes an electric drive of the screw type and four inductive sensors which allow the detection of the presence of the door and the locked or unlocked position of the actuator as part of the control protocol. The door opening system is also used in the alarm conditions management protocol to assure the safety of the user. All input and output required to achieve the door actuator system are listed on the electrical block diagram as: Lock Door Contactor, Unlock Door Contactor, Door closed Lower Sensor (S2), Door closed Upper Sensor (S1), Door Locked Sensor (S4) and Door Unlocked sensor (S3).

The Ozone power supply (116) includes a full wave rectifier, an oscillator circuit and a high voltage transformer. The output of the transformer is hooked up to the ozone generator (22). The power supply (116) is mounted as a resonator using the non-ideal characteristics of the high voltage transformer. The PLC 108 controls the ozone production and ensures by way of the ozone monitor 104 that the concentration desired for sterilization is achieved and maintained throughout the sterilization cycle. All input and output required by the Ozone Generation System is listed on the diagram as: Oxygen Supply Valve (26), Ozone to Chamber Valve (29a), Ozone Dump to Catalyst Valve (29b), Ozone Monitor Zeroing & Cycle counter), High Voltage Control, High Voltage Current Limiter, Ozone High Voltage Overload sensor Rectifier High Temperature Sensor, Ozone High Voltage Not Running Sensor and Ozone monitor Failure Sensor.

Ozone to Chamber Valve (29a) and Ozone Dump to Catalyst Valve (29b) are driven by an Electronic Solenoid Power Damper) (117). This apparatus prevents over-heating of the valves.

The oxygen supply system includes the oxygen supply valves 21 and 26, as well as a 350 mbar (gauge) maximum gas pressure regulator 24. The sensors and regulators are an integral part of the alarm condition protocol to ensure the protection of the user. Inputs used for the alarm condition are listed on the electrical block diagram as: Oxygen High Pressure Sensor and Oxygen Low Pressure Sensor.

The control system is provided with a user interface 118. In the preferred embodiment, this interface includes a touch-sensitive liquid crystal display (LCD) screen 118, a printer 119 for performance reports and a communications port 153 (Series RS-232) allowing the user to receive and transmit information necessary for use of the apparatus. It will be readily apparent to the person skilled in the art that other types of user interfaces can be used such as touch-sensitive pads, keyboards, or the like, and other types of communications interfaces. Thermal printer status inputs appear on the electrical block diagram as: Printer Off Line Sensor and Printer Out of Paper.

The system in accordance with the invention is capable of producing a relative humidity level higher than 95%.

The energy needed to evaporate the water during the humidification phase is taken from many sources. It is taken principally from the water and the structure of the humidifier unit. This contributes to a further cooling of the humidifier, and its contents. In effect, at 20° C., water boils up to an absolute pressure of 23.3 mbar and at 35° C., water boils up to an absolute pressure of 56.3 mbar. The vacuum in the sterilization chamber is preferably adjusted at a pressure where the boiling temperature of water is lowered below the temperature in the sterilization chamber. That boiling temperature may be so low that the temperature of water inside the humidifier decreases rapidly and, depending on the energy available from the surrounding structure and liquid, the water in the humidifier chamber may freeze before it gets vaporized. The evaporation process cooled the humidifier to a point where room air moisture condenses and may also freezes to the external surface of the humidifier. This can be avoided in another preferred embodiment by heating the external surface of the humidifier sufficiently to keep the exterior of the humidifier unit and the water inside the humidifier chamber at room temperature. This is achieved with a heating arrangement (not illustrated) which will be readily apparent to the person of skill in the art. Also, because of the high level of relative humidity achieved inside the chamber there is condensation on chamber inner surfaces and inside water vapour piping. To reduce water condensation the bottom of the chamber, the door and the water vapour piping also heated.

The water vapour generated in the humidifier unit increases the relative humidity in the sterilization chamber. The humidification phase is continued until the relative humidity of the gas surrounding the medical instruments contained in the packaging pouches and containers reaches a minimum of 85%, preferably 100%. For a sterilization chamber of an approximate volume of 125 liters, the water vapour admission increases the pressure to about 50 mbar in the sterilization chamber. This value is an approximation because it is temperature dependent.

Oxygen/ozone-containing sterilization gas is injected into the humidified sterilization chamber at a temperature close to ambient. The ozone-containing gas is not heated as in the prior art. For optimum operation of a sterilizer in accordance with the invention and having a 125 liters chamber, a system is preferably used which is capable of generating an ozone flow of about 1 to 3 liters per minute containing about 85 mg/l of ozone to obtain at least of total of 10600 mg of ozone for each of the fillings of the sterilization chamber.

In another preferred process, humidification of the sterilization chamber is carried out by a pair of atomizers. The water is supplied to each of the atomizers from a water tank hooked up to the drinking water supply or a purified water supply. Ozone is supplied to the atomizers from an ozone accumulation tank. The atomizers are made of ozone oxidation resistant material, and are installed directly in the sterilization chamber. When the vacuum level is reached in the sterilization chamber, the atomizers release water and ozone. The ozone is moistened inside the atomizer. The ozone/atomized water mixture penetrates the sterilization chamber. Injecting the water into the sterilization chamber under vacuum has the immediate effect of evaporating the water. The sterilization chamber operating temperature is 25 to 40° C., a temperature at which water evaporates at pressures of 31.7 to 73.8 mbar. Thus, the water becomes vapour due to the vacuum created by the vacuum pump. The resulting ozone/water vapour mixture penetrates the material to be sterilized.

Changes and modifications in the specifically described embodiments can be carried out without departing from the scope of the invention which is intended to be limited only by the scope of the appended claims.

The invention claim is:

1. A method for sterilizing an article in a sterilization gas atmosphere, comprising the steps of:
    (a) providing a sterilization chamber;
    (b) placing the article into the sterilization chamber;
    (c) applying a vacuum to the sterilization chamber for adjusting the pressure in the sterilization chamber to a sterilization pressure at which the boiling point of water in the sterilization chamber is lowered to a temperature below the temperature in the sterilization chamber;
    (d) supplying an amount of water to the sterilization chamber for humidifying the atmosphere in the sterilization chamber until a preselected humidification level is reached;
    (e) supplying ozone-containing sterilization gas to the sterilization chamber until a preselected ozonation level is reached;
    (f) stopping the supplying of water and ozone-containing sterilization gas and sealing the sterilization chamber for maintaining the sterilization pressure, humidification level and ozonaton level, in the sterilization chamber for a preselected treatment period; and
    (g) releasing the vacuum in the sterilization chamber, wherein prior to step (c), the temperature of the article is equalized with the temperature of an atmosphere in the sterilization chamber to prevent condensation of water on the article due to localized temperature differentials when the relative humidity in the sterilization chamber appwacbes saturation and wherein the step of equalizing includes multiple steps of evacuating the sterilization chamber and intermediate steps of flushing the sterilization chamber with oxygen or ambient air.

2. The method of claim 1, wherein the oxygen or ambient air is at ambient temperature.

3. The method of claim 1, wherein the step of equalizing includes equalizing the temperature of the article, the atmosphere in the sterilization chamber, and any components and materials in contact with the atmosphere.

4. The method of claim 3, operated at a temperature of 25 to 35° C.

5. The method of claim 4, wherein the vacuum pressure is between 0.5 and 2 mbar.

6. The method of claim 5, wherein the amount of water is selected to achieve a level of humidity of at least 95%.

7. The method of claim 6, wherein the (c) to (f) are repeated a number of times sufficient to ensure complete sterilization of the article.

8. The method of claim 1, operated at a temperature in the sterilization chamber of 25 to 40° C.

9. The method of claim 1, wherein the vacuum pressure is between 0.1 and 10 mbar.

10. The method of claim 1, wherein the amount of water is selected to achieve a level of humidity in the sterilization chamber of 85 to 100%.

11. The method of claim 1, wherein the steps (c) to (f) are repeated at least once.

12. The method of claim 1, further comprising the step of passing all gases evacuated from the sterilization chamber through a means for destroying ozone to prevent emission of ozone to the atmosphere.

* * * * *

UNITED STATES PATENT AND TRADEMARK OFFICE
CERTIFICATE OF CORRECTION

| | |
|---|---|
| PATENT NO. | : 7,128,872 B2 |
| APPLICATION NO. | : 10/005786 |
| DATED | : November 8, 2001 |
| INVENTOR(S) | : Richard Turcot et al. |

It is certified that error appears in the above-identified patent and that said Letters Patent is hereby corrected as shown below:

Title Page, item [75] Inventors, delete "Dufresue" and insert therefor --Dufresne--;

Column 14, line 23, delete "ozonaton" and insert therefor --ozonation--;

Column 14, line 31 (claim 1), delete "appwacbes" and insert therefor --approaches--.

Signed and Sealed this

Twelfth Day of February, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,128,872 B2 | Page 1 of 1 |
| APPLICATION NO. | : 10/005786 | |
| DATED | : October 31, 2006 | |
| INVENTOR(S) | : Richard Turcot et al. | |

It is certified that error appears in the above-identified patent and that said Letters Patent is hereby corrected as shown below:

Title Page, item [75] Inventors, delete "Dufresue" and insert therefor --Dufresne--;

Column 14, line 23, delete "ozonaton" and insert therefor --ozonation--;

Column 14, line 31 (claim 1), delete "appwacbes" and insert therefor --approaches--.

This certificate supersedes the Certificate of Correction issued February 12, 2008.

Signed and Sealed this

Fourth Day of March, 2008

JON W. DUDAS
*Director of the United States Patent and Trademark Office*